United States Patent [19]

Alt

[11] Patent Number: 5,116,606
[45] Date of Patent: May 26, 1992

[54] SKIN TREATMENT METHOD AND SOLUTION

[76] Inventor: John P. Alt, 2100 S. Federal Hwy., Fort Lauderdale, Fla. 33316

[21] Appl. No.: 527,813

[22] Filed: May 24, 1990

Related U.S. Application Data

[63] Continuation-in-part of Ser. No. 321,216, Mar. 9, 1989.

[51] Int. Cl.$^5$ .................. A61K 7/06; A61K 7/075
[52] U.S. Cl. ......................... 424/70; 424/680; 514/859; 514/864; 514/880; 514/881
[58] Field of Search ............... 424/70, 680; 514/859, 514/880, 881, 864

[56] References Cited

U.S. PATENT DOCUMENTS

| | | | |
|---|---|---|---|
| 711,263 | 10/1902 | Robertson | 424/70 |
| 3,579,632 | 5/1971 | Sonnen | 424/70 |
| 3,689,669 | 9/1972 | Piette | 424/583 |
| 3,928,251 | 12/1975 | Bolich, Jr. et al. | 252/545 |
| 4,088,760 | 5/1978 | Benson et al. | 424/242 |
| 4,174,296 | 11/1979 | Kass | 424/70 |
| 4,515,778 | 5/1985 | Kastell | 424/70 |
| 4,606,913 | 8/1986 | Aronson et al. | 424/63 |
| 4,660,580 | 4/1987 | Hoch et al. | 424/70 |
| 4,719,194 | 1/1988 | Patel | 424/70 |
| 4,765,975 | 8/1988 | Iovanni et al. | 424/70 |
| 4,971,784 | 11/1990 | Holzel et al. | 424/70 |

FOREIGN PATENT DOCUMENTS

| | | | |
|---|---|---|---|
| 202299 | 11/1984 | Japan | 424/70 |

OTHER PUBLICATIONS

Article "Extracellular Androgen Binding Protein", C. Wayne Bardin, et al Ann. Rev. Physiol, 1981, 43:189–98.

Article,—J. Soc. Cosmetic Chemists 1965 16:431–446, "The Hormonal Background of the Skin", Dodds.

*Primary Examiner*—Thurman K. Page
*Assistant Examiner*—Amy Hulina
*Attorney, Agent, or Firm*—Herbert L. Lerner; Laurence A. Greenberg

[57] ABSTRACT

Skin treatment solution and method having an aqueous, dissociable, sodium salt solution with a pH in the 6.0–8.0 range and containing enough sodium to substantially remove testosterone from the skin area to which the solution is applied topically. The sodium salt solution has sodium chloride as the major salt constituent and much smaller amounts of choline chloride, inositol, pantothenic acid and vitamin E, as well as a surfactant and sodium fluoride as a preservative.

6 Claims, No Drawings

SKIN TREATMENT METHOD AND SOLUTION

CROSS-REFERENCE TO RELATED APPLICATION

This application is a continuation-in-part of my co-pending U.S. patent application Ser. No. 07/321,216, filed Mar. 9, 1989.

FIELD OF THE INVENTION

This invention relates to a method of treating a selected area of a person's skin, such as to facilitate hair growth or to treat acne, by substantially removing testosterone from that skin area and to an aqueous solution for use in such method of skin treatment.

BACKGROUND OF THE INVENTION

It is well known that certain physiological manifestations are caused by an accumulation of particular chemicals in the metabolic system. More specifically, skin is an active site of androgen metabolism and responds to the removal of androgens for the treatment of acne and oily skin as discussed in U.S. Pat. No. 4,088,760 Benson et al. There is evidence to indicate that testosterone is involved in the pathogenesis of acne as well as other androgen related conditions.

Another of these conditions is pattern baldness in males wherein hair follicles, primarily on the crown of the head, shrink in size, producing an ever thinner and thinner hair until ultimately many follicles shrink to a point where they can no longer produce a hair, i.e., they become dormant. Individuals expressing pattern baldness begin to lose their hair very early in life, often in their twenties. It is well documented that male pattern baldness is a type of sex-influenced inheritance, with the allele for pattern baldness being dominant in males and recessive in females. As is true of many genetic mechanisms, however, the precise mechanism of regulation is not thoroughly understood.

Over the past several years, extracellular androgen-binding macro molecules have been identified that are distinct from the intracellular androgen-receptors. The best characterized are the testosterone-extradiol binding globulin (TeBG) from serum and the androgen binding protein (ABP) from the testis itself, as disclosed in "Extracellular Androgen Binding Proteins" by Bardin et al in Ann. Rev. Physiol, 1981, pages 189-198. A variety of in vivo studies have suggested that TeGB-bound testosterone is less available for expression of biological activity than is the free steroid, although the number of steroid receptor sites and structural relationships among sub-units thought to be present has not been established.

Neutral salts have pronounced effects on the solubility of globular proteins. These effects are caused by the changes in the tendency of dissociable groups on the protein to ionize, when the concentration of neutral salts is greatly increased, a protein may be completely precipitated, an effect called "salting out". This salting out process seems to rejuvenate hair follicles that are producing a hair, allowing them to return to their normal size. This salting out process also appears to stimulate long dormant follicles (i.e., follicles no longer producing a hair) to again produce a hair and over time grow back to normal size.

Although the absence of circulating androgens is believed fundamentally necessary to counter expression of baldness in males, other factors are also important. Basically, there are two different methods by which biochemical activities are controlled. One is genetic regulation and the other enzymatic regulation. Most often these regulatory mechanisms function as feedback control systems that continually monitor a cell's biochemistry and make corrections as needed. But, on occasion, substances from without also control intracellular biochemical reactions by inhibiting or activating one or more of the intracellular control systems.

My prior U.S. patent application Ser. No. 07/321,216 relates to facilitating hair growth by substantially removing testosterone from a selected area of a person's scalp, using an aqueous shampoo solution containing a dissociable sodium salt. One ingredient of that solution, lecithin, was thought to act principally as an emulsifier. In storage, after two or three months the lecithin began to decompose and the invention began to lose its effectiveness.

I have since discovered that the lecithin in my prior solution was of much greater importance than just working as an emulsifier. The omission of the lecithin from the invention resulted in a serious thinning of the hair growing on the crowns of the heads of men who were the test group for the invention. Contained in the solutions of my prior patent application for the invention was soy-extracted lecithin, which is a mixture of phosphatidyl choline with lesser amounts of phosphatidyl inositol, phosphatidyl serine, phosphatidyl ethanolamine and vitamins A, C and E.

Choline is normally present in animals in the form of phosphatides. It has been shown that humans require from 0.5 to 1.0 grams of choline per day, an order of magnitude more nearly resembling that of individual amino acids rather than that of vitamins. While it is generally believed that a large portion of the choline is present as acetylcholine, a neurotransmitter, a delicate balance is maintained between acetylcholine and choline, a vasodilator, by means of the enzymes choline acetylase and choline esterase which can acetylate to acetylcholine or hydrolyze to free choline when necessary. According to Holland & Grieg (1952), the formation and breakdown of acetylcholine may be related to cell permeability.

It has been shown that young mice deficient in inositol suffer an inhibition of growth and loss of hair, both of which are corrected by inositol supplementation. The spectacled-eyed condition in rats due to loss of hair about the eyes is also a result of inositol insufficiency. No corresponding tests have been found for humans but since inositol is present in both normal rat and normal human hair in about the same ratio as in other tissues one might speculate on additional similarities.

Wide distribution of pantothenic acid in animal and plant tissues is indicative of the fundamental role that pantothenic acid plays in cellular metabolism. In particular, symptoms due to pantothenic acid deficiency in experimental animals are frequently seen in epithelial tissues. Skin symptoms such as cornification, desquamation, and alopecia frequently occur. It is generally believed that pantothenic acid is necessary for the proper metabolism of inositol.

The function of vitamin E in animals remains at best uncertain. It is thought to act as an antioxidant thereby preventing cell membrane damage of the unsaturated fat component. Without vitamin E in the invention, the scalp became dry, scaly and very oily and the hair became quite brittle. Following the inclusion of vitamin E into the invention, the scalp completely recovered from its prior dry, scaly, oily condition and the hair became soft, flexible, and vibrant to the look and touch. Therefore, vitamin E is necessary for the success of this invention.

SUMMARY OF THE INVENTION

The present invention embodies the following important changes in the treatment method and solution of my aforementioned earlier application:

(1) to avoid possible contaminants in soy-extracted lecithin and to enable the choline/inositol ratio to be selected, the present invention used purified choline chloride and purified inositol in place of lecithin;

(2) the solution of the present invention contains pantothenic acid for the proper metabolism of the inositol now present in the solution;

(3) vitamin E, which I have determined to be the only vitamin essential to the successful use of the present solution and method, is substituted for the vitamins present in the soy-extracted lecithin of my aforementioned earlier application; and (4) the present invention uses sodium fluoride as a preservative in place of sodium ascorbate and sodium citrate, which were in the solution of my aforementioned earlier application and were found to render the invention less effective.

One primary aspect of the present invention is concerned with facilitating hair growth by substantially removing testosterone from a selected area of a person's scalp.

In accordance with this aspect of the invention, the following steps are carried out, preferably:

(1) apply to the selected scalp area for 3-5 minutes a dissociable sodium salt solution with a pH of 6.0-7.5 and containing purified water, shampoo concentrate, sodium chloride, sodium fluoride (a preservative), choline and inositol, a source of pantothenic acid, vitamin E and polysorbate-80 (as a surfactant);

and (2) rinse that scalp area with water.

Optionally, a conditioner having the same ingredients, except that the shampoo concentrate is omitted, may be applied to the treated scalp area after that area has dried naturally after being rinsed.

In accordance with this aspect, an object of this invention is to provide a novel method of treating a person's scalp to facilitate hair growth.

Also, in accordance with this aspect, another object of this invention is to provide a novel aqueous, dissociable sodium salt solution for application to a person's scalp to facilitate hair growth.

A further object of this invention, in accordance with this aspect, is to provide a novel shampoo containing a dissociable sodium salt solution for facilitating hair growth.

Another primary aspect of this invention is concerned with treating acne by substantially removing testosterone from a selected area of a person's skin. In accordance with this aspect of the invention, the same dissociable salt solution as used in the shampoo but with inositol omitted may be used as a facial scrub to treat acne.

Further objects and advantages of the present invention will become evident from the following detailed description of the presently-preferred embodiments.

DETAILED DESCRIPTION

Hair Growth

The first step in treating a selected area of a person's scalp to facilitate hair growth, particularly a person with male pattern baldness, is to apply an ionic shampoo solution of sufficient strength to substantially remove testosterone from the treated scalp area but without damage to proliferating tissue.

Preferably, the shampoo solution contains:

| | |
|---|---|
| purified water | 64% |
| shampoo concentrate | 32% |
| sodium chloride | 3.4% |
| Polysorbate-80 | 0.4% |
| inositol | 0.08% |
| sodium fluoride | 0.07% |
| choline chloride | 0.04% |
| pantothenic acid | 0.01% |
| vitamin E | 200 IU/gal. |

The foregoing percentages are by weight. The shampoo concentrate is CYCLORL ALC-2, a baby shampoo concentrate sold by Cyclo Corporation, 7500 N.W. 66th Street, Miami, Fla. 33166, and having the active ingredients: water, PEG-80 Sorbitan laurate, sodium trideceth sulfate, lauroamphoglycinate, Laureth-13 carboxylate, PEG-150 distearate, cocamidopropyl hydroxylsultaine, and citric acid.

The shampoo solution is prepared by mixing the water and shampoo concentrate in the weight percentages just stated and adding the NaF to this mixture. Next, the inositol is added to this mixture, which is thoroughly agitated to insure complete mixing. In a separate container, the Polysorbate-80 and vitamin E are combined, stirred, and allowed to stand for about 10 minutes, after which the choline chloride is added. This mixture of Polysorbate-80, vitamin E and choline chloride is stirred to produce a uniform blend. The mixture of water, shampoo concentrate, sodium fluoride and inositol is added to the sodium chloride in a separate container and mixed thoroughly with it, after which the mixture of Polysorbate-80, vitamin E and choline chloride is slowly added with constant stirring for maximum ease in preparation and uniform consistency of the final shampoo solution.

For normal usage, 0.085 ounces of this shampoo is applied to previously wetted hair and scalp. Subsequently, the scalp is gently massaged to insure uniform distribution of the solution over the entire area, as is characteristic of standard shampooing practice. Massage is also desirable in aiding increased blood flow to the cells of the epithelial layer. The shampoo is maintained on the scalp for a time period of 3-5 minutes, which is sufficient for maximal interaction between the ionics, the testosterone and the TeBG inherently present in the epithelial tissues.

At the end of this 3-5 minutes interval, the contacted area of the scalp is rinsed with water.

Preferably, the next step is to apply an ionic hair conditioner solution to the same area of the scalp. Preferably, this hair conditioner solution contains by weight:

| | | |
|---|---|---|
| purified water | - | 96% |
| sodium chloride | | 3.4% |
| Polysorbate-80 | | 0.4% |
| inositol | | 0.08% |

| | |
|---|---|
| sodium fluoride | 0.07% |
| choline chloride | 0.04% |
| pantothenic acid | 0.01% |
| vitamin E | 200 IU/gal. |

This conditioner solution is the same as the shampoo solution except that the shampoo concentrate is replaced by an equal amount of water.

After the conditioner is applied, the hair is allowed to dry naturally since forced drying tends to interfere with the continued ionic action of the conditioner.

Action of the conditioner is thought to further the testosterone removal action initiated by the shampoo. However, effective results have been obtained using only the shampoo and not the conditioner.

The efficacy of the above-specified shampoo treatment alone and the efficacy of the shampoo and hair conditioner treatments in sequence, as described, were tested on adult male persons with a serious thinning of the hair on the crown area of the head. Within one month of using daily applications of the foregoing shampoo solution there occurred a substantial thickening of the hair in the crown area of the head and also totally new hair growth, particularly in the hairline area on the forehead. While it is desirable to postulate an action mechanism, current knowledge of the physiological "modus operandi" of this particular invention may best be described as a synergism between the ionic component and the vitamin like substances, namely the pantothenic acid, choline chloride and inositol. It is thought that the electrolytes are able to extract water and water insoluble impurities from the hair follicles thereby facilitating the action of the vitamin like substances on the cleansed epithelial tissues. Since identified vitamins are known to participate in enzymatic reactions of a highly complex nature either as precursors of enzymes or as substrates, it is conceivable that the vitamin like substances in this invention may act similarly.

In both the shampoo and the hair conditioner it is highly desirable to maintain the pH of the aqueous solution within the 6.0-8.0 range, preferably from 6.0-7.5 for most effective results.

The shampoo and the hair conditioner each may also contain fragrances and/or coloring as desired.

Acne Treatment

In accordance with the present invention, a facial scrub solution for application to a person's skin to treat acne is provided which contains purified water, dissociable sodium salts and the vitamin like substances previously mentioned. Preferably, this facial scrub solution is the same as the previously specified shampoo solution except that the inositol is omitted and it is prepared the same way except that inositol is not added to the initial mixture of water, shampoo concentrate and sodium fluoride. The pH of this solution may be within the 6.0-8.0 range, with the 6.0-7.5 range preferred.

This facial solution is intended for use in the conventional manner. A small amount (0.05 ounces) is applied to the skin which has been previously rinsed with water. The preparation is massaged into the skin with the fingertips to facilitate a deep cleansing action after which the face is again rinsed with water and patted dry. Two facial scrubs a day are recommended.

For best results, daily application of the facial scrub solution or of the shampoo and conditioner is recommended to make the testosterone removal as thorough as possible and to stimulate blood flow and proliferation of new cells in the treated area. None of these ingredients acts as a drug, and they are safe. No deleterious side effects have been detected.

I claim:

1. A method of treating a selected area of a person's skin which comprises applying topically to said area of skin an aqueous solution consisting essentially of the following percentages by weight of the named ingredients:

| | |
|---|---|
| sodium chloride | 3.4% |
| inositol | 0.08% |
| choline chloride | 0.04% |
| pantothetic acid | 0.01% |
| Vitamin E | 200 IU/gal | wherein the pH of said solution is within the 6.0-7.5 range.

2. A method according to claim 1 wherein said solution is a shampoo solution having purified water and shampoo concentrate.

3. A method according to claim 1 wherein said solution is a scalp conditioner solution containing purified water and a surfactant.

4. A method according to claim 1 wherein said solution is applied as an acne medicament.

5. A method of treating a person's scalp to facilitate hair growth which comprises the steps of:

applying to a selected area of the scalp a shampoo solution, consisting of ingredients having substantially the following concentrations by weight:

| | |
|---|---|
| sodium chloride | 3.4% |
| sodium fluoride | 0.07% |
| choline chloride | 0.04% |
| inositol | 0.08% |
| pantothenic acid | 0.01% |
| vitamin E | 200 IU/gal | wherein the remainder of the solution consists essentially of water, shampoo concentrate and surfactant;

and, after a time period sufficient for said solution to substantially remove testosterone from said area of the scalp, rinsing said area of the scalp with water.

6. A method according to claim 5 wherein said surfactant is Polysorbate-80 in a concentration of substantially 0.4 by weight.

* * * * *